United States Patent
Herdman et al.

(10) Patent No.: US 9,593,245 B2
(45) Date of Patent: *Mar. 14, 2017

(54) CONTROLLED RELEASE, WOOD PRESERVING COMPOSITION WITH LOW-VOLATILE ORGANIC CONTENT FOR TREATING IN-SERVICE UTILITY POLES, POSTS, PILINGS, CROSS-TIES AND OTHER WOODEN STRUCTURES

(71) Applicant: OSMOSE UTILITIES SERVICES, INC., Peachtree City, GA (US)

(72) Inventors: Douglas J. Herdman, Fayetteville, GA (US); Jun Zhang, Peachtree City, GA (US); Thomas Pope, Newnan, GA (US); Randy C. Marquardt, Fayetteville, GA (US)

(73) Assignee: Osmose Utilities Services, Inc., Peachtree City, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/257,632

(22) Filed: Sep. 6, 2016

(65) Prior Publication Data
US 2016/0369109 A1 Dec. 22, 2016

Related U.S. Application Data

(63) Continuation of application No. 15/062,415, filed on Mar. 7, 2016, now Pat. No. 9,464,196, which is a continuation of application No. 14/305,659, filed on Jun. 16, 2014, now Pat. No. 9,303,169.

(51) Int. Cl.
| | |
|---|---|
| C09D 5/14 | (2006.01) |
| A01N 59/20 | (2006.01) |
| B27K 3/12 | (2006.01) |
| B27K 3/22 | (2006.01) |

(52) U.S. Cl.
CPC .............. *C09D 5/14* (2013.01); *A01N 59/20* (2013.01); *B27K 3/12* (2013.01); *B27K 3/22* (2013.01); *B27K 2240/20* (2013.01)

(58) Field of Classification Search
CPC . B27K 3/005; B27K 3/02; B27K 3/12; B27K 3/22; B27K 3/30; B27K 3/163; B27K 3/32; B27K 2200/00; A01N 59/14; A01N 59/20; C09D 5/14; B05D 7/06
See application file for complete search history.

(56) References Cited

U.S. PATENT DOCUMENTS

| | | | |
|---|---|---|---|
| 3,007,844 A | 11/1961 | Schulz | |
| 4,656,060 A | 4/1987 | Krzyzewski | |
| 4,797,281 A | 1/1989 | Broome et al. | |
| 4,804,494 A | 2/1989 | Egerton et al. | |
| 5,084,280 A | 1/1992 | West | |
| 5,342,438 A | 8/1994 | West | |
| 6,110,263 A | 8/2000 | Goettsche et al. | |
| 6,306,202 B1 | 10/2001 | West | |
| 6,352,583 B1 | 3/2002 | Goettsche et al. | |
| 8,221,797 B2 | 7/2012 | Zhang et al. | |
| 8,221,897 B2 | 7/2012 | Muroga et al. | |
| 8,603,576 B2 | 12/2013 | Leach et al. | |
| 8,722,198 B2 | 5/2014 | Richardson et al. | |
| 8,778,407 B2 | 7/2014 | Zhang et al. | |
| 9,303,169 B2 | 4/2016 | Herdman et al. | |
| 2004/0258767 A1 | 12/2004 | Leach et al. | |
| 2005/0095663 A1 | 5/2005 | Young et al. | |
| 2005/0118280 A1 | 6/2005 | Leach et al. | |
| 2006/0057300 A1 | 3/2006 | Cui et al. | |
| 2006/0288904 A1 | 12/2006 | Leach et al. | |
| 2008/0193640 A1 | 8/2008 | Zhang et al. | |
| 2010/0183868 A1 | 7/2010 | Zhang et al. | |
| 2013/0164362 A1 | 6/2013 | Richardson et al. | |

FOREIGN PATENT DOCUMENTS

| | | |
|---|---|---|
| EP | 0539619 A1 | 5/1993 |
| WO | 9623636 A1 | 8/1996 |

OTHER PUBLICATIONS

American Wood Protection Association, Standard A3-14, "Standard Methods for Determining Penetration of Preservatives and Fire Retardants—Method 2—Method for Determining Penetration of Copper-Containing Preservatives," 2014, p. 1.
American Wood Protection Association, Standard E10-12, "Standard Method of Testing Wood Preservatives by Laboratory Soil-Block Cultures," 2014, 11 pp.
EPA Method 8260B, "Volitile Organic Compounds by Gas Chromatography/Mass Spectrometry (GC/MS)," 1996, Revision 2.
International Search Report and Written Opinion dated Dec. 23, 2015 for related PCT Patent Application No. PCT/US15/034174.
Morrell, J.J. et al, Oregon State University—Utility Pole Research Cooperative 33rd Annual Report, 2013, 140 pp.
Related U.S. Appl. No. 14/305,659 and the prosecution history thereof.
Related U.S. Appl. No. 15/062,415 and the prosecution history thereof.

*Primary Examiner* — Anthony J Green
(74) *Attorney, Agent, or Firm* — Troutman Sanders, LLP; James E. Schutz; Alexis N. Simpson

(57) ABSTRACT

Disclosed herein are compositions comprising a dispersion of solid particles of a substantially insoluble copper compound in an amount from 0.001% to 10% by weight of the composition; a boron-containing compound, a fluoride-containing compound, or a combination thereof; and an aqueous carrier; wherein the composition has a viscosity of 125 to 425 tenths of a millimeter (tmm) as measured using a penetrometer, and wherein at least 20% of the particles of the composition comprise particles having particle size greater than 25 microns. Also disclosed herein are methods of making and using the same.

20 Claims, No Drawings

CONTROLLED RELEASE, WOOD PRESERVING COMPOSITION WITH LOW-VOLATILE ORGANIC CONTENT FOR TREATING IN-SERVICE UTILITY POLES, POSTS, PILINGS, CROSS-TIES AND OTHER WOODEN STRUCTURES

CROSS-REFERENCE TO RELATED APPLICATIONS

This application is a continuation application of (and claims the benefit of priority of) U.S. patent application Ser. No. 15/062,415 (filed 7 Mar. 2016, and issued 11 Oct. 2016 as U.S. Pat. No. 9,464,196), which is a continuation of U.S. patent application Ser. No. 14/305,659 (filed 16 Jun. 2014, and issued 5 Apr. 2016 as U.S. Pat. No. 9,303,169), the contents of both of which are incorporated by reference herein in their entireties.

FIELD

This disclosure relates to wood preserving compositions for the supplemental or remedial treatment of wood in service, such as utility poles and railroad ties.

BACKGROUND

Wood and/or cellulose based products exposed in an outdoor environment are biodegradable, primarily through attack by microorganisms. As a result, they will decay, weaken in strength, and discolor. The microorganisms causing wood deterioration include brown rots such as *Postia placenta, Gloeophyllum trabeum* and *Coniophora puteana*, white rots such as *Irpex lacteus* and *Trametes versicolor*, dry rots such as *Serpula lacrymans* and *Meruliporia incrassata* and soft rots such as *Cephalosporium, Acremonium*, and *Chaetomium*. In addition, wood is still subject to attack by wood-inhabiting insects, such as termites, beetles, ants, bees, wasps and so on. Wood preservatives are well known for preserving wood and extend the service life of wood products including decking boards, fence posts, utility poles, railroad ties, permanent wood foundation, and other cellulose-based materials, such as paper, plywood, particleboard, textiles, rope, etc., against organisms responsible for the deterioration of wood.

Utility poles and railroad cross ties are wooden structures that are traditionally pressure treated with wood preservative chemicals, such as chromated copper arsenate (CCA), pentachlorophenol, copper naphthenate or creosote. Pressure treatment with preserving chemicals can certainly prevent utility poles or railroad cross ties from fungal and termite attack and the pressure treatment can usually last for 30 to 40 years. However, the wood preserving chemicals can only penetrate through most of the sapwood portion of the wood species and rarely penetrate the heartwood portion. This will cause insufficient treatment and insufficient chemical absorption. In addition, improper treating practices may also cause poor treatment and insufficient chemical loadings. A direct consequence of the poor penetration and insufficient chemical loading is that, once the treated utility poles are placed in service, often times a small percentage of poles show early failure and subsequent strength loss. As a result, a supplemental or remedial treatment is needed to offer the protection for those poles that show early failures. In older poles, the preservative chemicals in the outer sapwood zone will gradually decline due to water leaching, ultraviolet degradation, chemical alteration or physical damage. As a result, external decay or termite attack may develop on the outer surface, and therefore there is an additional need for supplemental or remedial treatments to further extend the service life of aging utility poles and other wooden structures.

Preservative groundline treatments provide an economical extension to the useful life of utility poles. Experience has shown that groundline decay can be postponed almost indefinitely in cases where periodic inspection and maintenance programs are in effect. External treatments on utility poles and other wooden structures are typically applied below the ground level either as pastes or grease-type compositions that are brushed on the wood surface, and then covered with a moisture resistant barrier, or as self-contained ready-made preservative bandages. In both cases, the goal is to supplement the original preservative treatment to prevent or arrest surface decay. Protection is dependent upon the ability of the active ingredients to penetrate and remain in the treatment zone, and is limited to the depth of penetration. In addition, the composition must possess satisfactory physical properties, such as viscosity, spreadability, adherence, etc.

Historically, oilborne preservatives have been used for treating in-service utility poles and other wooden structures. Traditional oilborne preservatives included petroleum oils, creosote, copper naphthenate and pentachlorophenol. However, the use of oilborne supplemental preservatives is declining due to concerns of worker exposure to the organic solvents and leaching of the organic solvents into the environment. Furthermore, the organic solvents, including No. 2 fuel oil, have recently experienced unprecedented price increases making them cost prohibitive for the manufacture of supplemental/remedial wood preservative compositions.

Current, known commercially established preservatives for the after protection of in-service utility poles and other wooden structures contain copper or copper combined with boron and/or fluoride as their active biocides. Copper compounds, such as copper sulfate, copper carbonate and copper hydroxide, are generally known to be effective biocides as wood preservatives. Preferred copper compounds are generally insoluble and therefore must be solubilized to be effective in supplemental wood preservative compositions. This is typically accomplished by complexing the copper compounds with ammonia, acids or amines. Known copper complexes used in the field of wood preservation include copper naphthenate, water-dispersible copper naphthenate, copper ethanolamine, ammoniacal copper citrate, alkaline copper quaternary and others. Sodium fluoride and sodium borate are the most commonly used biocides in remedial preservative compositions. The sodium salts of boron and fluoride are able to penetrate further through the wood structure due to their water solubility and mobility.

Although prior art compositions for the remedial treatment of utility poles and other wooden structures have been shown to be effective in extending the useful life of wood products in-service, there are several problems that exist with current preservative compositions.

One limitation of using oil or water dilutable copper complexes is that they can readily leach from wood. Leaching of copper from wood can be further increased by the presence of oil solvents present in utility poles or cross ties from initial treatment with pentachlorophenol, creosote or copper naphthenate. Elevated moisture levels commonly found within in-service poles and ties, particularly near or below groundline, can also increase the leaching rate of water dilutable copper complexes found in current preservative paste compositions.

The leaching of the copper component from current paste compositions is a concern from both a performance and environmental perspective. Depletion of the copper by leaching will ultimately compromise the long term bioefficacy of the supplemental or remedial formulation, and the leached copper causes concern that the environment surrounding the treated structure will be contaminated. It has been established that copper is extremely toxic to fish and other aquatic organisms at very low concentrations. Concerns over copper leaching from supplemental wood preservative compositions are such that their use is often limited or even restricted in areas of standing water or near water ways.

The uncontrolled mobility of the copper component from current paste compositions is a further concern from a performance standpoint. Water soluble copper complexes provide an uncontrolled dose to the wooden structure to be preserved by quickly dispersing beyond the intended zone of protection within the wooden structure and rapidly depleting the copper reservoir contained within paste composition diminishing the ability of the treatment to provide prolonged periods of protection from the action of decay and wood destroying insects such as termites.

In addition, the copper component of current supplemental wood preservative compositions is not protective against some species of copper-tolerant wood decay fungi, often located in the Gulf-Coast region of the U.S. Generally, higher loadings of copper are required in remedial compositions containing soluble forms of copper and/or a co-biocide is incorporated into the composition to afford protection against copper-tolerant decay fungi.

Finally, complexing copper to impart solubility can be expensive. Generally, high levels of the complexing agents are required to solubilize copper compounds. For example, 2 to 4 moles of a complexing or copper-solubilizing agent, such as monoethanolamine, for example, are required to complex 1 mole of copper. In the case of ammonia, 4 moles are required to complex 1 mole of copper. This can add considerable cost to the formulated remedial preservative compositions. In addition, oilborne copper naphthenate and other oil-based compositions generally require the use of No. 2 fuel oil as a carrier and are therefore extremely susceptible to large variations in cost.

Examples of supplemental or remedial preservative compositions for the afterprotection of wood in-service can be found in the following literature.

U.S. Pat. No. 5,342,438 to West discloses a non-water dilutable remedial wood preservative containing copper derived from an amine-inorganic copper complex, combined with at least one sodium salt selected from the group consisting of sodium borate and sodium fluoride in a ratio of 2 to 120 parts of the sodium salt for each part of copper in the preservative.

U.S. Pat. No. 6,110,263 to Goettsche teaches a process for the afterprotection of wood, which comprises treating the wood with an effective wood preserving amount of a wood preservative composition comprising a copper compound, a polyamine or alkanolamine having at least two nitrogen atoms, and an inorganic fungicide, the treatment being effected by means of a bandaging process, an inoculation injection process, a borehole process or a paste process.

U.S. Pat. No. 5,084,280 to West claims a paste composition for preserving wood which contains as its only active wood preservation ingredients a mixture of 10-90% by weight of a water-dispersible copper naphthenate and 90-10% by weight of borax.

U.S. Pat. No. 6,352,583 to Goettsche discloses a wood preservative for the supplemental protection of wood, consisting essentially of one or more copper compounds, one or more alkanolmonoamines and one or more complexing organic carboxylic acids or ammonium or alkali metal salts of said complexing organic carboxylic acids.

U.S. Pat. No. 6,306,202 to West teaches a water soluble fixed copper-borax wood preservative composition which comprises a fixed copper compound selected from the group consisting of copper oxides, copper hydroxide, basic copper carbonate, basic copper sulfate, and copper oxychloride combined in water with sodium tetraborate decahydrate wherein the fixed copper compound concentration ranges from 0.01 parts to 0.20 parts for each part of sodium tetraborate decahydrate.

U.S. Pat. No. 8,221,797 to Zhang discloses a wood preservative composition for the supplemental or remedial treatment of in-service poles, posts, piling, cross ties and other wooden structures. The wood preservative composition comprises copper 8-hydroxyquinolate (oxine copper) in combination with a boron compound or a fluoride compound wherein the copper-8-quinolinolate is about 0.001% to about 2% by weight with a weight ratio of a boron or fluoride compound of 1:1. The preferred form of oxine copper in this invention is a fine particulate, such that is found in dispersions through the milling process. Although it is not the most preferred, the composition of this invention can also be formulated into an oil-borne paste- or grease-like formulation where the oxine copper is solubilized with an organic solvent.

This invention discloses a supplemental or remedial wood preservative composition which solves the problems identified with current, known compositions and addresses the need for a more environmentally friendly technology for the afterprotection of in-service wooden structures. This need is solved by the subject matter disclosed herein.

SUMMARY

The present invention provides an aqueous wood preservative paste composition comprising a dispersion of particles of a copper compound; a boron-containing compound; an aqueous carrier; and a thickening agent wherein the particles of the copper compound are present in an amount of about 0.001% to about 10% by weight of the composition. In one embodiment, the aqueous wood preservative paste composition is formulated to provide a controlled release of copper ions in a fungitoxic amount into an interior portion of the wooden structure.

The wood preservative composition of the present invention contain no more than about 36, 30, 20, 10, 5, 2 or 1 grams VOCs (volatile organic compounds) per volume of the wood preservative coating. As used herein, the unit "grams VOC per volume of the wood preservative coating" means the mass (in grams) of VOCs per volume of a dehydrated wood preservative composition. In contrast, the mass VOC per volume of the wood preservative composition refers to the mass of VOCs per volume of the wood preservative composition, including the aqueous carrier. In one preferred embodiment, VOCs are not detectable by gas chromatography/mass spectrometry (GC/MS), according to EPA Method 8620, Volatile Organic Compounds by Gas Chromatography Mass Spectrometry (GC/MS).

In one embodiment, the wood preservative composition is formulated as a thixotropic paste.

The wood preservative paste compositions of the present invention are preferably formulated such that at least 20, 30, 40 or 50% of the particles of the paste composition comprise particles with diameters greater than about 25 microns. In another embodiment, the wood preservative compositions of the present invention are preferably formulated such that less than 10, 15 or 20% of the particles of the paste compositions comprise particles with diameters below about 100 microns. Conversely, the wood preservative compositions of the present invention are preferably formulated such that more than 80, 85 or 90% of the particles of the paste compositions comprise particles with diameters of about 100 microns or greater.

The wood preservative compositions of the present invention are produced by a method comprising the step of blending solid particles of a substantially insoluble copper compound comprising a particle size diameter between 0.01 and 25 microns; a boron-containing compound; an aqueous carrier; and a thickening agent, to produce a paste composition with a viscosity of between 125 and 425 tenths of a millimeter (tmm) as measured using a penetrometer and, in a preferred embodiment, producing a paste composition wherein at least 20, 30, 40 or 50% of the particles of the paste composition comprise particles with diameters greater than about 25 microns; wherein less than 10, 15 or 20% of the particles of the paste compositions comprise particles with diameters below about 100 microns; or wherein more than 80, 85 or 90% of the particles of the paste compositions comprise particles with diameters of about 100 microns or greater.

In a preferred embodiment of the present invention, the solid particles of a substantially insoluble copper compound comprise a particle size diameter between 0.1 and 10 microns, more preferably between 0.1 and 5 microns and most preferably between 0.1 and 2 microns.

The present invention also provides a method of delivering a fungitoxic amount of copper ion to an interior portion of a wooden product comprising. These methods comprise the step of applying an aqueous paste composition of the present invention to a wooden structure, such as a utility pole, pole, piling, railroad tie or other wooden structure, or the like. The application step may comprise brushing the aqueous paste composition onto the surface of a wooden structure or other methods of applying a remedial treatment known in the art or described herein. In a preferred embodiment, the interior portion of the wooden structure is an interior region of the wooden structure extending from but excluding the surface of the wooden structure to about ¼ inch from the surface of the wooden structure. In one embodiment, the fungitoxic amount of copper ions that penetrate the wood surface and migrate to an interior portion of a wooden structure is about 0.04 pounds per square foot (PCF). In another embodiment, the fungitoxic amount delivered to an interior portion of a wooden structure is not more than 5, 10, 20, 30 or 50% greater than 0.04 PCF.

The wood preservative compositions disclosed herein may also optionally contain one or more organic biocides. In one embodiment, the organic biocide is a fungicide, insecticide, moldicide, bactericide, or algaecide, or combinations thereof. In a preferred embodiment, the organic biocide is a quaternary ammonium compound, a triazole compound, an imidazole compound, an isothiazolone compound, or a pyrethroid compound, or combination thereof. In another embodiment, the organic biocide is imidacloprid, fipronil, cyfluthrin, bifenthrin, permethrin, cypermethrin, chlorpyrifos, iodopropynyl butylcarbamate (IPBC), chlorothalonil, 2-(thiocyanatomethylthio) benzothiazole, alkoxylated diamines or carbendazim.

In a preferred embodiment, the boron-containing compound is a boric acid, a metal borate, a sodium borate, or a potassium borate. In one embodiment, the sodium borate is sodium tetraborate decahydrate, sodium tetraborate pentahydrate, or disodium octaborate tetrahydrate (DOT). In another embodiment, the metal borate is calcium borate, borate silicate, aluminum silicate borate hydroxide, silicate borate hydroxide fluoride, hydroxide silicate borate, sodium silicate borate, calcium silicate borate, aluminum borate, boron oxide, magnesium borate, iron borate, copper borate or zinc borate.

The present invention also provides a supplemental or remedial wood preserving composition which comprises a copper compound combined with at least one boron compound or fluoride compound, or combinations thereof, which has good stability, low toxicity to animal and plant life and high biocidal activity against wood decay fungi and termites. The composition additionally comprises organic fungicides and/or termiticides to further enhance the bio-efficacy.

The present invention also provides remedial paste compositions and methods for preservation of wooden poles, railroad ties and other wooden structures against both fungal and termite attack and methods of treating wooden poles, railroad ties and other wooden structures with the wood preservative compositions of the present invention comprising the step of either dip or brush application of the paste compositions onto and/or into the wooden poles, railroad ties and other wooden structures. In one embodiment, the methods for preservation of wooden structures comprises the step of applying the remedial paste compositions of the present invention to cuts, holes or other injuries to previously pressure treated wood.

The present invention provides a preventive treatment for standing wood utility poles, piles, lumber, timber, posts, ties and other exterior wooden structures including those standing in or in proximity to the ground that are susceptible to attack by decay and soft rot fungi, termites, carpenter ants, carpenter bees or wood boring beetles.

For prevention or control of exterior infestations in utility poles, piles, posts, and other wooden structures standing in the ground, excavate the soil away from the structure to a depth of 18 to 24 inches. Thoroughly clean and remove any decay or damaged wood from the treatment zone before applying the preservative. In one embodiment, the wood preservative compositions of the present invention are applied at rates from ¹⁄₁₆" to ⅜" thick to the area that is about 2" above ground line down to a depth of up to 24". In one embodiment, the application rate and treatment zone is dependent on the severity of condition, age and condition of the original preservative. In another embodiment, the treatment zone, after treatment, plus an area 2 inches above is covered with an impermeable moisture barrier.

The invention also discloses a method for preparing a water-dilutable supplemental or remedial wood preserving composition which comprises either mixing, blending or milling the insoluble copper compound in water.

The wood preservative compositions of the present invention do not comprise one or more copper-solubilizing agents, such as ammonia, an ammonium salt, an amine, mono- or polyalkanolamines.

The present invention also provides a method for preparing the wood preservative composition of the present invention comprising the step of maintaining the viscosity of the wood preservative composition between 275 and 425 tenths of a millimeter (tmm). In a preferred embodiment, the viscosity is maintained between 300 and 400 tmm. In a more preferred embodiment, the viscosity is maintained between 320 and 340 tmm. The wood preservative compositions of the present invention comprise a copper compound that is substantially insoluble in the aqueous carrier. The copper or copper compounds such as cuprous oxide (a source of copper (I) ions), cupric oxide (a source of copper (II) ions), copper hydroxide, copper carbonate, basic copper carbonate, copper oxychloride, copper dimethyldithiocarbamate, copper omadine, copper borate, copper residues (copper metal byproducts) or any suitable copper source can be used. These particles exhibit a relatively low solubility in water. In a preferred embodiment, the copper compound is copper hydroxide, copper carbonate, or basic copper carbonate. In one embodiment, the wood preservative composition comprises between about 0.001% to about 10% copper atoms by weight of the composition. In another embodiment, the wood preservative composition comprises between about 0.01% to about 2% copper atoms by weight of the composition. In a preferred embodiment, the wood preservative composition comprises between about 0.1% to about 1% copper atoms by weight of the composition. In a more preferred embodiment, the composition contains between 1 and 5% copper atoms by weight of the composition. In another preferred embodiment, the composition contains between 1 and 3% copper atoms by weight of the composition. In preferred embodiments, the wood preservative compositions of the present invention contain between about 1 and 5%; about 1 and 3%; about 0.01 and 2% and about 0.1 and 1% copper atoms by weight of the composition.

In preferred embodiments, the wood preservative composition of the present invention do not comprise one or more copper-solubilizing agents, including but not limited to ammonia, an ammonium salt, an amine, mono- or polyalkanolamines.

The copper compounds suitable for the wood preservative compositions of the present invention are substantially insoluble in the aqueous carrier.

The boron-containing compound of the wood preservative compositions of the present invention are preferably boric acid, a metal borate, a sodium borate, or a potassium borate. In a preferred embodiment, the sodium borate is sodium tetraborate decahydrate, sodium tetraborate pentahydrate, or disodium octaborate tetrahydrate (DOT). The metal borate is preferably calcium borate, borate silicate, aluminum silicate borate hydroxide, silicate borate hydroxide fluoride, hydroxide silicate borate, sodium silicate borate, calcium silicate borate, aluminum borate, boron oxide, magnesium borate, iron borate, copper borate or zinc borate. In one embodiment, the weight ratio of the boron compound to copper—is about 1:1. In a preferred embodiment, the weight ratio of the boron compound to copper is about 10:1. In a more preferred embodiment, the weight ratio of the boron compound to copper is about 25:1. In the most preferred embodiment, the weight ratio of the boron compound to copper is about 50:1.

The wood preservative compositions of the present invention may further comprise a fluoride-containing compound. In one embodiment, the fluoride compound is sodium fluoride, potassium fluoride, calcium fluoride, copper fluoride, iron fluoride, or magnesium fluoride. In one embodiment, the weight ratio of the fluoride compound to copper is about 1:1. In a preferred embodiment, the weight ratio of the fluoride compound to copper is about 10:1. In a more preferred embodiment, the weight ratio of the fluoride compound to copper is about 50:1. In the most preferred embodiment, the weight ratio of the fluoride compound to copper is about 500:1. In another embodiment, the weight ratio of the fluoride compound to copper is between about 1:1 and about 500:1. In another embodiment, the weight ratio of the fluoride compound to copper is between about 1:1 and about 50:1. In yet another embodiment, the weight ratio of the fluoride compound to copper is between about 1:1 and about 10:1.

The wood preservative compositions of the present invention may further comprise one or more organic biocides. The organic biocides suitable for use with the present invention may include a fungicide, insecticide, moldicide, bactericide, or algaecide, or combinations thereof. In another embodiment, the organic biocide is a quaternary ammonium compound, a triazole compound, an imidazole compound, an isothiazolone compound, or a pyrethroid compound, or combination thereof. In a preferred embodiment, the organic biocide is imidacloprid, fipronil, cyfluthrin, bifenthrin, permethrin, cypermethrin, chlorpyrifos, iodopropynyl butylcarbamate (IPBC), chlorothalonil, 2-(thiocyanatomethylthio) benzothiazole, alkoxylated diamines or carbendazim. In one embodiment, the weight ratio of the organic biocide is about from 0.001% to 10% by weight. In another embodiment, the weight ratio of the organic biocide is about from 0.005% to 5% by weight. In yet another embodiment, the weight ratio of the organic biocide is about from of 0.01% to 1% by weight.

The wood preservative compositions of the present invention are preferably formulated as pastes using an organic thickener, an inorganic thickener or a combination of organic and inorganic thickeners. In a preferred embodiment, the organic thickener is cellulose-derived, such as a cellulose ester or a cellulose ether. Preferably, the cellulose ester is cellulose nitrate, sulfate, cellulose phosphate, cellulose nitrite, cellulose xanthate, cellulose acetate, cellulose formate or combination thereof. Preferably, the cellulose ether is methylcellulose, ethylcellulose, propylcellulose, benzylcellulose, carboxymethylcellulose, hydroxyethylcellulose, hydroxypropylcellulose, hydroxybutylcellulose, cyanoethylcellulose, or carboxyethylcellulose. In one embodiment, the thickening agent is about 0.01% to 50% by weight in the composition. In another embodiment, the thickening agent is about 0.5% to 10% by weight in the composition.

In a preferred embodiment, the inorganic thickener of the wood preservative compositions of the present invention is a clay. Preferably, the clay is attapulgite, dickite, saponite, montmorillonite, nacrite, kaolinite, anorthite, halloysite, metahalloysite, chrysotile, lizardite, serpentine, antigorite, beidellite, stevensite, hectonite, smecnite, nacrite, sepiolite, montmorillonite, sauconite, stevensite, nontronite, saponite, hectorite, vermiculite, illite, sericite, glauconite-montmorillonite, roselite-montmorillonite, bentonite, chlorite-vermiculite, illite-montmorillonite, halloysite-montmorillonite, or kaolinitemontmorillonite. More preferably, the clay is attapulgite, hectorite, bentonite, montmorillonite, sauconite, smecnite, stevensite, beidellite, nontronite, saponite, hectorite, vermiculite, nacrite, or sepiolite. In one embodiment, the inorganic thickener is about 0.5% to about 30% by weight.

The wood preservative compositions of the present invention may also further comprise a drying retardant or a humectant, or both.

The wood preservative composition of the present invention may be packaged in containers, wraps, bandages and the like. In one embodiment, the container is a can, a bucket or a bag. In one embodiment the compositions of the present invention packaged in a container have a viscosity between 175 and 375 tenths of a millimeter (tmm). In a preferred embodiment, the viscosity is between 200 and 300 tmm. In a more preferred embodiment, the viscosity is between 210 and 250 tmm.

The present invention also provides a method for remedial treatment of wood, comprising the step of applying the composition of the present invention to wood. In a preferred method, the wood is an in-service wood product, such as a utility pole, a railroad tie or wooden bridge. Preferably, the compositions of the present invention are applied by brush or spray. Preferably, the composition is applied to wood to a thickness of between 1/32 and 3/4 inches. In a more preferred embodiment, the composition is applied to wood to a thickness of between 1/16 and 1/2 inches. In a most preferred embodiment, the composition is applied to wood to a thickness of between 1/16 and 1/4 inches.

The boron-containing compound of the wood preservative compositions of the present invention are preferably boric acid, a metal borate, a sodium borate, or a potassium borate. In a preferred embodiment, the sodium borate is sodium tetraborate decahydrate, sodium tetraborate pentahydrate, or disodium octaborate tetrahydrate (DOT). The metal borate is preferably calcium borate, borate silicate, aluminum silicate borate hydroxide, silicate borate hydroxide fluoride, hydroxide silicate borate, sodium silicate borate, calcium silicate borate, aluminum borate, boron oxide, magnesium borate, iron borate, copper borate or zinc borate. In one embodiment, the weight ratio of the boron compound to copper—is about 1:1. In a preferred embodiment, the weight ratio of the boron compound to copper is about 10:1. In a more preferred embodiment, the weight ratio of the boron compound to copper is about 25:1. In the most preferred embodiment, the weight ratio of the boron compound to copper is about 50-:1.

The wood preservative compositions of the present invention may further comprise a fluoride-containing compound. In one embodiment, the fluoride compound is sodium fluoride, potassium fluoride, calcium fluoride, copper fluoride, iron fluoride, or magnesium fluoride. In one embodiment, the weight ratio of the fluoride compound to copper is about 1:1. In a preferred embodiment, the weight ratio of the fluoride compound to copper is about 10:1. In a more preferred embodiment, the weight ratio of the fluoride compound to copper is about 50:1. In the most preferred embodiment, the weight ratio of the fluoride compound to copper is about 500:1. In another embodiment, the weight ratio of the fluoride compound to copper is between about 1:1 and about 500:1. In another embodiment, the weight ratio of the fluoride compound to copper is between about 1:1 and about 50:1. In yet another embodiment, the weight ratio of the fluoride compound to copper is between about 1:1 and about 10:1.

The wood preservative compositions of the present invention may further comprise one or more organic biocides. The organic biocides suitable for use with the present invention may include a fungicide, insecticide, moldicide, bactericide, or algaecide, or combinations thereof. In another embodiment, the organic biocide is a quaternary ammonium compound, a triazole compound, an imidazole compound, an isothiazolone compound, or a pyrethroid compound, or combination thereof. In a preferred embodiment, the organic biocide is imidacloprid, fipronil, cyfluthrin, bifenthrin, permethrin, cypermethrin, chlorpyrifos, iodopropynyl butylcarbamate (IPBC), chlorothalonil, 2-(thiocyanatomethylthio) benzothiazole, alkoxylated diamines or carbendazim. In one embodiment, the weight ratio of the organic biocide is about from 0.001% to 10% by weight. In another embodiment, the weight ratio of the organic biocide is about from 0.005% to 5% by weight. In yet another embodiment, the weight ratio of the organic biocide is about from of 0.01% to 1% by weight.

The wood preservative compositions of the present invention are preferably formulated as pastes using an organic thickener, an inorganic thickener or a combination of organic and inorganic thickeners. In a preferred embodiment, the organic thickener is cellulose-derived, such as a cellulose ester or a cellulose ether. Preferably, the cellulose ester is cellulose nitrate, sulfate, cellulose phosphate, cellulose nitrite, cellulose xanthate, cellulose acetate, cellulose formate or combination thereof. Preferably, the cellulose ether is methylcellulose, ethylcellulose, propylcellulose, benzylcellulose, carboxymethylcellulose, hydroxyethylcellulose, hydroxypropylcellulose, hydroxybutylcellulose, cyanoethylcellulose, or carboxyethylcellulose. In one embodiment, the thickening agent is about 0.01% to 50% by weight in the composition. In another embodiment, the thickening agent is about 0.5% to 10% by weight in the composition.

In a preferred embodiment, the inorganic thickener of the wood preservative compositions of the present invention is a clay. Preferably, the clay is attapulgite, dickite, saponite, montmorillonite, nacrite, kaolinite, anorthite, halloysite, metahalloysite, chrysotile, lizardite, serpentine, antigorite, beidellite, stevensite, hectonite, smecnite, nacrite, sepiolite, montmorillonite, sauconite, stevensite, nontronite, saponite, hectorite, vermiculite, illite, sericite, glauconite-montmorillonite, roselite-montmorillonite, bentonite, chlorite-vermiculite, illite-montmorillonite, halloysite-montmorillonite, or kaolinitemontmorillonite. More preferably, the clay is attapulgite, hectorite, bentonite, montmorillonite, sauconite, smecnite, stevensite, beidellite, nontronite, saponite, hectorite, vermiculite, nacrite, or sepiolite. In one embodiment, the inorganic thickener is about 0.5% to about 30% by weight.

The wood preservative compositions of the present invention may also further comprise a drying retardant or a humectant, or both.

The wood preservative composition of the present invention may be packaged in containers, wraps, bandages and the like. In one embodiment, the container is a can, a bucket or a bag. In one embodiment the compositions of the present invention packaged in a container have a viscosity between 175 and 375 tenths of a millimeter (tmm). In a preferred embodiment, the viscosity is between 200 and 300 tmm. In a more preferred embodiment, the viscosity is between 210 and 250 tmm.

The present invention also provides a method for remedial treatment of wood, comprising the step of applying the composition of the present invention to wood. In a preferred method, the wood is an in-service wood product, such as a utility pole, a railroad tie or wooden bridge. Preferably, the compositions of the present invention are applied by brush or spray. Preferably, the composition is applied to wood to a thickness of between 1/32 and 3/4 inches. In a more preferred embodiment, the composition is applied to wood to a thickness of between 1/16 and 1/2 inches. In a most preferred embodiment, the composition is applied to wood to a thickness of between 1/16 and 1/4 inches.

The present invention also provides a method for preparing the wood preservative composition of the present invention comprising the step of maintaining the viscosity of the wood preservative composition between 275 and 425 tenths of a millimeter (tmm). In a preferred embodiment, the viscosity is maintained between 300 and 400 tmm. In a more preferred embodiment, the viscosity is maintained between 320 and 340 tmm.

DETAILED DESCRIPTION

Unless stated otherwise, such as in the examples, all amounts and numbers used in this specification are intended to be interpreted as modified by the term "about". Likewise, all elements or compounds identified in this specification, unless stated otherwise, are intended to be non-limiting and representative of other elements or compounds generally considered by those skilled in the art as being within the same family of elements or compounds.

As used herein, the term "micronized" means a particle size in the range of 0.001 to 25 microns. As used herein, the term "particle size" means the largest axis of the particle, and in the case of a generally spherical particle, the largest axis is the diameter. Furthermore, it should be understood that "micronized" does not refer only to particles which have been produced by the finely dividing, such as by mechanical grinding, of materials which are in bulk or other form. Micronized particles can also be formed by other mechanical, chemical or physical methods, such as, for example, formation in solution, with or without a seeding agent, grinding or impinging jet.

The micronized copper particles disclosed in U.S. Patent Application Publication No. 2005/0118280 are hereby specifically incorporated by reference, in their entirety.

As used herein, "copper-solubilizing agents" mean any agent that promotes the solubility of copper metal or a copper compound in an aqueous carrier. Copper-solubilizing agents include, but are not limited to ammonia and ammonium salts, amines, and alkanolmonoamines having between 2 to 18 carbon atoms, such as monoalkanolmonoamines, dialkanolmonoamines, and trialkanolmonoamines, and mixtures thereof. Examples include monoethanolamine, diethanolamine, triethanolamine, 3-aminopropanol, monoisopropanolamine, 4-aminobutanol, monomethylethanolamine, dimethylethanolamine, triethylethanolamine, monoethylethanolamine, N-methyldiethanolamine and mixtures thereof.

Disclosed herein is a supplemental/remedial composition for wood and a method for use thereof in treatment of in-service wooden products, more particularly utility poles, railroad ties, wooden bridges. The composition comprises copper with a boron compound or fluoride compound. The composition imparts to the treated wood resistance to both fungi and insects. The composition can additionally comprise an organic fungicide/termiticide.

In an effort to limit the level of volatile organic compounds (VOCs) being released into the atmosphere and to minimize worker exposure, the Environmental Protection Agency (EPA) published the architectural coatings rule on 1988 under authority of the Clean Air Act. The purpose of this rulemaking was to reduce the VOCs emitted from architectural and industrial maintenance coatings thus limiting the amount of VOCs that manufacturers can put in their products. Remedial preservative paste formulations are defined by EPA as architectural coatings and below ground wood preservatives. The VOC limit established by EPA for below ground wood preservatives is 550 grams of VOC per liter of coating. Individual States such as Pennsylvania, New York and California (South Coast Air Quality Management District) have established a more stringent allowable VOC limit for below ground wood preservatives of 350 grams per liter of coating. The present invention provides compositions containing no more than 36, 30, 20, 10, 5, 2 or 1 grams volatile organic compounds (VOCs) per liter of the composition. In a preferred embodiment, VOCs are not detectable by gas chromatography/mass spectrometry (GC/MS). In another preferred embodiment, VOCs are not detectable by gas chromatography according to EPA Method 8620, Volatile Organic Compounds by Gas Chromatography Mass Spectrometry (GC/MS), which is incorporated herein by reference in its entirety.

The compositions of the present invention have a broad spectrum of bio-efficacy against wood decay fungi, including, brown rot fungi, white rot fungi, and soft rot fungi. Non-limiting examples of brown rot fungi include: *Coniophora puteana, Serpula lacrymans, Antrodia vaillantii, Gloeophyllum trabeum, Gleoeophyllum sepiarium, Lentinum lepideus, Oligoporus placenta, Meruliporia incrassate, Daedalea quercina, Postia placenta*. Non-limiting examples of white rot fungi include: *Trametes versicolor, Phanerochaete chrysosporium, Pleurotus ostreatus, Schizophyllum commune, Irpex lacteus*. Some non-limited examples of soft rot fungi are *Chaetomium globosum, Lecythophora hoffmannii, Monodictys putredinis, Humicola alopallonella, Cephalosporium, Acremonium*, and *Chaetomium*.

The compositions of the present invention are also effective against a broad range of insects and marine borer, including termites, beetles, and wood-boring insects. Non-limiting examples of termites include drywood termites such as *Cryptotermes* and *Kaloterms*, and dampwood termites such as *Zootermopsis*, subterranean termites such as *Coptotermes, Mastotermes, Reticulitermes, Schedorhinotermes, Microcerotermes, Microtermes*, and *Nasutitermes*. Non-limiting examples of beetles include those in families such as, for example, Anoniidae, Bostrychidae, Cerambycidae, Scolytidae, Curculionidae, Lymexylonidae, and Buprestidae.

The compositions of the present invention can be formulated into a waterborne paste- or grease-type of formulation, if desired, such that the formulation has an adhesive nature and is easy to apply to a desired location.

The present invention includes copper. The preferred form of copper for preparation of the aqueous paste compositions of the present invention is a fine particulate, such that is found in dispersions through a milling process or the like. Methods for preparing milled substantially insoluble biocidal particulates that can be used in aqueous wood preservative compositions that can be applied to a wood product by vacuum and/or pressure treatment to effectively penetrate and preserve wood may be found in U.S. Patent Application Publication Nos. 2004/0258767, 2005/0118280 and 2006/0288904 to Leach and Zhang. The weight ratio of copper in the composition varies from about 0.001% to about 10% by weight. The preferred range of weight ratio of copper in the composition varies from about 0.1% to about 1% by weight.

The present invention also comprises a boron compound, a fluoride compound or both. The boron compound can be either water soluble or water insoluble. Non-limiting examples of water soluble boron compounds include boric acid, sodium borates, such as sodium tetraborate decahydrate, sodium tetraborate pentahydrate, and disodium octaborate tetrahydrate (DOT) and potassium borates. Non-limiting examples of water insoluble boron compounds include metal borate compounds such as calcium borate, borate silicate, aluminum silicate borate hydroxide, silicate borate hydroxide fluoride, hydroxide silicate borate, sodium silicate borate, calcium silicate borate, aluminum borate, boron oxide, magnesium borate, iron borate, copper borate and zinc borate.

Preferred boron compounds are water soluble boron compounds, such as boric acid and sodium tetraborate decahydrate, sodium tetraborate pentahydrate and disodium octaborate tetrahydrate (DOT).

The weight ratio of boron compound to copper can be in the range of from about 1:1 to about 500:1, the preferred weight ratio range is about 10:1 to about 200:1.

The present invention can also include a fluoride compound. Non-limiting examples of fluoride compounds include sodium fluoride, potassium fluoride, calcium fluoride, copper fluoride, iron fluoride, magnesium fluoride, and other metal compounds of fluoride. The preferred fluorides are sodium fluoride and potassium fluoride. The weight ratio of fluoride compound to copper can be in the range of from about 1:1 to about 1000:1, the preferred weight ratio range is about 10:1 to about 200:1.

The present composition optionally comprises one or more combinations of a organic biocides, such as quaternary ammonium compounds, triazole or imidazole compounds, isothiazolone compounds, pyrethroid compounds and other biocides such as imidacloprid; fipronil; cyfluthrin; bifenthrin; permethrin; cypermethrin; and chlorpyrifos, iodopropynyl butylcarbamate (IPBC); chlorothalonil; 2-(thiocyanatomethylthio) benzothiazole; alkoxylated diamines and carbendazim. When the organic biocide is used in the composition, the weight ratio of the organic biocide in the composition is generally in the range of from 0.001% to 10% by weight, with a preferred range of 0.005% to 5% by weight and a more preferred range of 0.01% to 1%.

Each of the organic biocides listed in Tables 1-4 of U.S. Patent Application Publication No. 2005/0118280 are hereby specifically incorporated by reference, in their entirety.

Non-limiting examples of quaternary ammonium compounds are: didecyldimethylammonium chloride; didecyldimethylammonium carbonate/bicarbonate; alkyldimethylbenzylammonium chloride; alkyldimethylbenzylammonium carbonate/bicarbonate; didodecyldimethylammonium chloride; didodecyldimethylammonium carbonate/bicarbonate; didodecyldimethylammonium propionate; N,N-didecyl-N-methyl-poly(oxyethyl) ammonium propionate.

Non-limiting examples of triazole or imidazole compounds are: 14[242,4-dichlorophenyl)-1,3-dioxolan-2-yl] methyl]-1H-1,2,4-triazole (azaconazole), 1-R2RS,4RS:2RS, 4SR)-4-bromo-2-(2,4-dichlorophenyptetrahydrofurfuryl]-1H-1,2,4-triazole (bromuconazole), 2RS,3RS;2RS,3SR)-2-(4-chlorophenyl)-3-cyclopropyl-1-(1H-1,2,4-triazol-1-yl) butan-2-ol (Cyproconazole), (2RS,3RS)-1-(2,4-dichlorophenyl)-4,4-dimethyl-2-(1H-1,2,4-triazol-1-yl) pentan-3-ol (diclobutrazol), cis-trans-3-chloro-444-methyl-2-(1H-1,2,4-triazol-1-ylmethyl)-1,3-dioxolan-2-yliphenyl 4-chlorophenyl ether (difenoconazole), (E)-(R5)-1-(2,4-dichloro-phenyl)-4,4-dimethyl-2-(1H-1,2,4-triazol-1-yl)pent-1-en-3-ol (diniconazole), (E)-®-1-(2,4-dichlorophenyl)-4,4-dimethyl-2-(1H-1,2,4-triazol-1-yl)pent-1-en-3-ol (diniconazole-M), (2RS, 3SR)-143-(2-chlorophenyl)-2,3-epoxy-2-(4-fluorophenyl)propyl]-1H-1,2,4-triazole (epoxycon-azole), (RS)-142-(2,4-dichlorophenyl)-4-ethyl-1,3-dioxolan-2-ylmethyli-1H-1,2,4-triazole (etaconazole), (RS)-4-(4-chlorophenyl)-2-phenyl-2-(1H-1,2,4-triazol-1-ylmethyl)butyronitrile (fenbuconazole), 3-(2,4-dichlorophenyl)-6-fluoro-2-(1H-1,2,4-triazol-1-yl) quinazolin-4(311)-one (fluquinconazole), bis(4-fluorophenyl)(methyl)(1H-1,2,4-triazol-1-ylmethyl)silane (flusi-lazole), (RS)-2,4'-difluoro-a-(1H-1,2,4-triazol-1-ylmethyl)benzhydryl alcohol (flutriafol), (2RS, 5RS; 2RS,5SR)-5-(2,4-dichlorophenyl)19arboxymet o-5-(1H-1,2,4-triazol-1-ylmethyl)-2-furyl 2,2,2-trifluoroethyl ether (furconazole), (2RS,5RS)-5-(2,4-dichlorophenyptetrahydro-541H-1,2,4-triazol-1-ylmethyl)-2-furyl 2,2,2-trifluoroethyl ether(furconazole-cis), (RS)-2-(2,4-dichloro-phenyl)-1-(1H-1,2,4-triazol-1-yl)hexan-2-ol(hexaconazole), 4-chlorobenzyl (EZ)—N-(2,4-dichlo-rophenyl)-2-(1H-1,2,4-triazol-1-yl) thioacetamidate (imibenconazole), (1RS,2SR,5RS; 1RS, 2SR,5SR)-2-(4-chlorobenzyl)-5-isopropyl-1-(1H-1,2,4-triazol-1-ylmethyl)cyclopentanol (ipconazole), (1RS,5RS; 1RS,5SR)-5-(4-chlorobenzyl)-2,2-dimethyl-1-(1H-1,2,4-triazol-1-ylmethyl)cyclopentanol (metconazole), (RS)-2-(4-chlorophenyl)-241H-1,2,4-triazol-1-ylmethyl)hexanenitrile (myclobutanil), (RS)-1-(2,4-dichloro-(3-propylphenethyl)-1H-1,2,4-triazole(penconazole), cis-trans-1-[2-(2,4-dichlorophenyl)-4-propyl-1,3-dioxolan-2-yl meth-yl]-1H-1,2,4-triazole (propiconazole), (RS)-2-[2-(1-chlorocyclopropyl)-3-(2-chloro phenyl)-2-hydroxypropyl-2,4-dihydro-1,2,4-triazole-3-thione(prothioconazole), 3-(2,4-dichlorophenyl)-2-(1H-1,2,4-triazol-1-yl)-quinazolin-4(311)-one (quinconazole), (RS)-2-(4-fluoro-phenyl)-1-(1H-1,2,4-triazol-1-yl)-3-(trimethylsilyl)propan-2-ol (simeconazole), (RS)-1-p-chlorophenyl-4,4-dimethyl-3-(1H-1,2,4-triazol-1-ylmethyl)pentan-3-ol (tebuconazole), propiconazole, (RS)-2-(2,4-dichlorophenyl)-3-(1H-1,2,4-triazol-1-yl)propyl 1,1,2,2-tetrafluoroethyl ether (tetracon-azole), (RS)-1-(4-chlorophenoxy)-3,3-dimethyl-1-(1H-1,2,4-triazol-1-yl) butan-2-one (triadime-fon), (1RS,2RS; 1RS,2SR)-1-(4-chlorophenoxy)-3,3-dimethyl-1-(1H-1,2,4-triazol-1-yl) butan-2-ol (triadimenol), (RS)-(E)-5-(4-chlorobenzylidene)-2,2-dimethyl-1-(1H-1,2,4-triazol-1-ylmethyl)cyclopentanol (triticonazole), (E)-(RS)-1-(4-chlorophenyl)-4,4-dimethyl-2-(1H-1,2,4-triazol-1-yl)pent-1-en-3-ol (uniconazole), (E)-(S)-1-(4-chlorophenyl)-4,4-dimethyl-241H-1,2,4-triazol-1-yl)pent-1-en-3-ol (uniconazole-P), and 2-(2,4-difluorophenyl)-1-(1H-1,2,4-triazole-1-yl)-3-trimethylsilyl-2-propanol. Other azole compounds include: amisulbrom, bitertanol, fluotrimazole, triazbutil, climbazole, clotrimazole, imazalil, oxpoconazole, prochloraz, triflumizole, azaconazole, simeconazole, and hexaconazole.

Non-limiting examples of isothiazolone compounds are: methylisothiazolinone; 5-chloro2-methyl-4-isothiazoline-3-one, 2-methyl-4-isothiazoline-3-one, 2-n-octyl-4-isothiazoline-3-one, 4,5-dichloro-2-n-octyl-4-isothiazoline-3-one, 2-ethyl-4-isothiazoline-3-one, 4,5-dichloro-2-cyclohexyl-4-isothiazoline-3-one, 5-chloro-2-ethyl-4-isothiazoline-3-one, 2-octyl-3-isothiazolone, 5-chloro-2-t-octyl-4-isothiazoline-3-one, 1,2-benzisothiazoline-3-one, preferably 5-chloro-2-methyl-4-isothiazoline-3-one, 2-methyl-4-isothiazoline-3-one, 2-n-octyl-4-isothiazoline-3-one, 4,5-dichloro-2-n-octyl-4-isothiazoline-3-one, 1,2-benzisothiazoline-3-one, etc., more preferably 5-chloro-2-methyl-4-isothiazoline-3-one, 2-n-octyl-4-isothiazoline-3-one, 4,5-dichloro-2-n-octyl-4-isothiazoline-3-one, 1,2-benzisothiazoline-3-one, chloromethylisothi-azolinone; 4,5-Dichloro-2-n-octyl-3 (2H)-isothiazolone; 1,2-benzisothiazolin3-one.

Non-limiting examples of pyrethroid compounds include acrinathrin, allethrin, bioallethrin, barthrin, bifenthrin, bioethanomethrin, cyclethrin, cycloprothrin, cyfluthrin, betacyfluthrin, cyhalothrin, gamma-cyhalothrin, lambda-cyhalothrin, cypermethrin, alphacypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, tau-fluvalinate, furethrin, imiprothrin, metofluthrin, permethrin, biopermethrin, transpermethrin, phenothrin, prallethrin, profluthrin, pyresmethrin, resmethrin, bioresmethrin, cismethrin, tefluthrin, terallethrin, tetramethrin, tralomethrin, transfluthrin, etofenprox, flufenprox, halfenprox, protrifenbute, silafluofen.

Preferred organic biocides are tebuconazole and bifenthrin.

The present invention also optionally comprises an aqueous type thickening agent. Aqueous organic polymer, aqueous emulsion, clay minerals, phosphate and the like are the aqueous type of thickening agents. Typical examples of aqueous organic polymers are cellulose derivatives including cellulose esters and ethers. Examples of cellulose esters are cellulose nitrate, sulfate, cellulose phosphate, cellulose nitrite, cellulose xanthate, cellulose acetate, cellulose formate, and cellulose esters with other organic acids. Examples of cellulose ethers are methylcellulose, ethylcellulose, propylcellulose, benzylcellulose, carboxymethylcellulose, hydroxyethylcellulose, hydroxypropylcellulose, hydroxybutylcellulose, cyanoethylcellulose, and 21 arboxymethylcellulose. The preferred cellulose derivatives are cellulose ethers such as hydroxyethylcellulose, hydroxypropylcellulose, carboxymethylcellulose and carboxyethylcellulose. The weight percentage of the cellulose derivative in the paste formulation is generally in the range of from about 0.01% to 50% with a preferred weight percentage of 0.1% to 20% and a more preferred weight percentage of 0.5% to 10%.

Furthermore, the present invention also optionally comprises about 0.5% to about 30% of an inorganic clay thickening agent, or a mixture of such thickening agents. The inorganic clay thickening agents include a fibrous structure type such as attapulgite clay and sepiolite clay, a non-crystal structure type such as allophone, and mixed layer structure type such as montmorillonite and kaolinte and the above layer structure types. Examples of inorganic clay minerals, but not limited to, are: attapulgite, dickite, saponite, montmorillonite, nacrite, kaolinite, anorthite, halloysite, metahalloysite, chrysotile, lizardite, serpentine, antigorite, beidellite, stevensite, hectonite, smecnite, nacrite and sepiolite, montmorillonite, sauconite, stevensite, nontronite, saponite, hectorite, vermiculite, smecnite, sepiolite, nacrite, illite, sericite, glauconite-montmorillonite, roselite-montmorillonite, Bentone 38 (hectorite) and Bentone 34 (bentonite), chlorite-vermiculite, illite-montmorillonite, halloysite-montmorillonite, kaolinitemontmorillonite. The clay minerals employed in the compositions of the present invention also contain exchangeable cations including, but not limited to, aluminum ions, protons, sodium ions, potassium ions, calcium ions, magnesium ions, lithium ions, and the like.

Among the above inorganic clay minerals, attapulgite, hectorite, bentonite, montmorillonite, sauconite, smecnite, stevensite, beidellite, nontronite, saponite, hectorite, vermiculite, nacrite, and sepiolite are particularly preferable for the present invention.

Further, these inorganic clay minerals show a good thickening effect and thixotopic property in comparison with other aqueous thickening agents. Therefore, they show a little sagging and also they are very easy to be rinsed out by water in comparison with organic thickening agents.

It should be appreciated that thickening agents other than described herein can be used.

Optionally, the present invention also includes chemical additives that retard the drying of the paste composition. These are usually a blend of several glycols, such as ethylene glycol, propylene glycol, polyethylene glycol, polypropylene glycol and their derivatives. By evaporating far more slowly than water, glycols or their derivatives can slow down the drying process of the paste composition. Humectants, such as glycerin and glycerol that absorb or hold water can also be added to retard or slow drying.

The preservative paste compositions of this invention can be applied by various processes of supplemental or remedial treatment or protection of in-service wooden structures. The compositions of this invention are suitable for incorporation into wraps or ready-to-use bandages, injection into voids or cavities by pressure or by gravity and solid rods or cartridges.

The paste compositions of this invention can be easily incorporated into a suitable support material to form a ready-to-use bandage or wrap that can applied to in-service utility poles and other wooden structures. Numerous support materials have been identified in literature and may include polymer films, fabrics, fiberglass, polyester fiber, polypropylene, porous polymer compositions and others that allow for the transfer or diffusion of preservative chemical from the bandage to the wood substrate. The paste composition may be applied to the support material by toweling, rolling, brushing and the like. The paste composition can be directly applied to the support material or may require the use of a binder or resin such as for example acrylate resins or PVC with plasticizers. To improve the adhesion between the paste compositions and support material the combination may be air-dried or dried in an oven at elevated temperatures.

The paste compositions of this invention may also be formed into solid rods by extrusion, rolling or pressing. Once sufficiently dried, the rods can be cut to length and inserted into predrilled holes in in-service utility poles or other wooden structures. As with the bandages or wraps, resins or binders may be added to improve the dimensional stability of the rods.

The paste compositions of this invention may be injected into internal voids or cavities through predrilled holes into in-service poles, posts, piling, cross-ties and other wooden structures by pressure processes or by gravity feed.

The following examples are provided to further describe certain embodiments of the invention, their preparation and application as remedial or supplemental paste preserving system, but are in no way meant to limit the scope of the invention. For the experiments, penetration testing has been found to be an effective means of establishing the consistency and shear stability of compositions of this invention. Penetrometers are generally used for consistency tests on a wide range of food products, cosmetics, greases, pastes and other solid to semisolid products. Penetrometers utilize a standard cone or needle that is released from the Penetrometer and allowed to drop feely into the sample for 5 seconds at constant temperature. The depth of penetration of the cone into the sample is measured in tenths of a millimeter (tmm) by the Penetrometer. It has been establish through testing that the preferable penetration of the compositions of this invention range from about 125 to 425 tmm when using a standard Penetrometer equipped with a 102.5 gram brass cone with a stainless steel tip. A more preferable range of consistency for the present invention is about 175 to 375 tmm and a consistency or shear stability of about 200 to 300 tmm is particularly preferable for the present invention.

The preferred viscosities of the thixotropic compositions of the present invention, during manufacture, is between 275 and 425 tenths of a millimeter (tmm) viscosity as measured using a penetrometer. More preferably the viscosities of the compositions of the present invention is between 300 and 400 tmm. Most preferably the viscosities of the compositions of the present invention is between 320 and 340 tmm.

The preferred viscosities of the thixotropic compositions of the present invention is between 175 and 375 tenths of a millimeter (tmm) viscosity as measured using a penetrometer. More preferably the viscosities of the compositions of the present invention is between 200 and 300 tmm. Most preferably the viscosities of the compositions of the present invention is between 210 and 250 tmm.

For determination of acceptability of viscosity, spreadability and adherence, compositions of the present invention can be rolled, troweled or brushed on wooden objects or more preferably to in-service utility poles, cross-ties or other wooden structures. Desirable compositions of the present invention should be self-supporting, have good spreadability such that the composition can be easily applied with a roller, trowel or brush without running or slumping off the wooden substrate or application tool and will easily adhere to a wooden substrate.

EXAMPLES

The Examples listed below illustrate methods for preparing various compositions and treating wood according to the invention. These Examples below, illustrate methods for preparing alternative versions of the inventive compositions. The methods described in these Examples are illustrative only, and are not intended to limit the invention in any manner and should not be construed to limit the scope of claims herein.

Example 1

A supplemental/remedial preservative paste composition was prepared by blending together in the order listed; 41.60 parts water, 6.00 parts of a fine copper dispersion comprised of 33.3% copper carbonate, 0.50 parts of a commercially available cellulose ether thickener, 43.70 parts sodium tetraborate decahydrate, and 8.20 parts attapulgite clay thickener. This remedial preservative paste contained 2.00 parts copper as derived from the fine copper carbonate dispersion for a weight ratio of 21.90 parts boron compound to 1.00 part copper.

The supplemental/remedial preservative paste composition formulated according to the above example was applied to a wooden substrate using a trowel and was found to have desirable physical properties including viscosity, spreadability and adherence for application to in-service utility poles, cross-ties and other wooden structures. Consequently, a preservative paste composition was obtained.

Example 2

A supplemental/remedial preservative paste composition was prepared by blending together in the order listed; 33.30 parts water, 3.00 parts of a fine copper dispersion comprised of 33.3% copper hydroxide, 10.00 parts glycerin, 2.00 parts of a commercially available cellulose ether thickener, 43.70 parts sodium tetraborate decahydrate, 1.00 part calcium sulfate filler and 7.00 parts attapulgite clay thickener. This remedial preservative paste contained 1.00 parts copper as derived from the fine copper hydroxide dispersion for a weight ratio of 43.70 parts boron compound to 1.00 part copper.

The supplemental/remedial preservative paste composition formulated according to the above example was applied to a wooden substrate using a trowel and was found to have desirable physical properties including viscosity, spreadability and adherence for application to in-service utility poles, cross-ties and other wooden structures. Consequently, a preservative paste composition was obtained.

Example 3

A supplemental/remedial preservative paste composition was prepared by blending together in the order listed; 30.24 parts water, 1.50 parts of a fine copper dispersion comprised of 33.3% basic copper carbonate, 10.00 parts glycerin, 3.00 parts of a commercially available cellulose ether thickener, 47.76 parts sodium tetraborate decahydrate, 1.50 part calcium sulfate filler and 6.00 parts attapulgite clay thickener. This remedial preservative paste contained 0.50 parts copper as derived from the fine basic copper carbonate dispersion for a weight ratio of 95.52 parts boron compound to 1.00 part copper.

The supplemental/remedial preservative paste composition formulated according to the above example was applied to a wooden substrate using a trowel and was found to have desirable physical properties including viscosity, spreadability and adherence for application to in-service utility poles, cross-ties and other wooden structures. Consequently, a preservative paste composition was obtained.

Example 4

A supplemental/remedial preservative paste composition was prepared by blending together in the order listed; 44.60 parts water, 0.02 parts bifenthrin, 3.00 parts of a fine copper dispersion comprised of 33.3% cupric oxide, 0.50 parts of a commercially available cellulose ether thickener, 43.70 parts sodium tetraborate decahydrate, and 8.2 parts attapulgite clay thickener. This remedial preservative paste contained 1.00 parts copper as derived from the fine cupric oxide dispersion for a weight ratio of 43.7 parts boron compound to 1.00 part copper.

Example 5

A supplemental/remedial preservative paste composition is prepared by blending together in the order listed; 34.00 parts water, 0.10 parts tebuconazole, 2.25 parts of a fine copper dispersion comprised of 33.3% basic copper carbonate, 10.00 parts glycerin, 3.00 parts of a commercially available cellulose ether thickener, 21.85 parts sodium tetraborate decahydrate, 21.85 parts boric acid, 1.00 part calcium sulfate filler and 6.0 parts attapulgite clay thickener.

This remedial preservative paste contains 0.75 parts copper as derived from the fine basic copper carbonate dispersion for a weight ratio of 58.27 parts boron compound to 1.00 part copper.

Example 6

A supplemental/remedial preservative paste composition was prepared by blending together in the order listed; 44.6 parts water, 0.50 parts of a commercially available cellulose ether thickener, 3.00 parts of a fine copper hydroxide dispersion comprised of 33.3% copper carbonate, 0.10 parts bifenthrin, 0.10 parts tebuconazole, 43.70 parts sodium tetraborate decahydrate, 6.5 parts attapulgite clay thickener and 1.5 parts calcium sulfate filler. This remedial preservative paste contained 1.00 parts copper as derived from the fine copper carbonate dispersion for a weight ratio of 43.7 parts boron compound to 1.00 part copper.

Penetration testing performed on the paste composition formulated according to the example above showed a penetration of 216 tmm. In addition, the supplemental/remedial preservative paste composition formulated according to the above example was applied to a wooden substrate using a trowel and was found to have desirable physical properties including viscosity, spreadability and adherence for application to in-service utility poles, cross-ties and other wooden structures. Consequently, a preservative paste composition was obtained.

Example 7

A supplemental/remedial preservative paste composition was prepared by blending together in the order listed; 37.00 parts water, 6.51 parts of a fine copper dispersion comprised of 31.6% cuprous oxide, 0.50 parts of a commercially available cellulose ether thickener, 50.00 parts sodium tetraborate decahydrate, and 6.00 parts attapulgite clay thickener. This remedial preservative paste contained 2.06 parts copper as derived from the fine cuprous oxide dispersion for a weight ratio of 24.27 parts boron compound to 1.00 part copper.

Penetration testing performed on the paste composition formulated according to the example above showed a penetration of 275 tmm. Further, the paste composition formulated according to the above example was brushed to 18 inches of the below ground section of an in-service utility pole. This paste was found to have desirable physical properties including viscosity, spreadability and adherence for application to in-service utility poles, cross-ties and other wooden structures. Consequently, a preservative paste composition was obtained.

Example 8

A supplemental/remedial preservative paste composition was prepared by blending together in the order listed; 44.6 parts water, 3.00 parts of a fine copper dispersion comprised of 33.3% copper carbonate, 0.70 parts pigmented dyes, 0.50 parts of a commercially available cellulose ether thickener, 43.70 parts sodium tetraborate decahydrate, and 7.50 parts attapulgite clay thickener. This remedial preservative paste contained 1.0 parts copper as derived from the fine copper carbonate dispersion for a weight ratio of 43.7 parts boron compound to 1.00 part copper.

Penetration testing performed on the paste composition formulated according to the example above showed a penetration of 211 tmm. Further, the paste composition formulated according to the above example was brushed to 18 inches of the below ground section of an in-service utility pole by an experienced preservative chemical applicator. This paste was found to have desirable physical properties including viscosity, spreadability and adherence for application to in-service utility poles, cross-ties and other wooden structures. Consequently, a preservative paste composition was obtained.

Further, the paste formed was applied to the surface of southern pine dimensional lumber that had previously been vacuum-pressure impregnated with water. The lumber was saturated with water to simulate moisture regimes that are typically present within the ground-line region of in-service utility poles and other wooden structures and that is required to provide mobility of the preservative paste into the wood substrate. The paste was applied at a thickness of a sixteenth of an inch and sealed to the lumber with a water impermeable wrap such that is used in commercial practice. At periods of 2, 4 and 6 weeks, small incremental wafers were taken from the treated sections of the lumber. Wafers were sprayed with the copper penetration reagent Chrome Azurol S in accordance with American Wood Protection Association's (AWPA) Standard A3-08 (which is incorporated herein by reference in its entirety), Method 2, Method for Determining Penetration of Copper-Containing Preservatives. It was determined by visual inspection that copper had penetrated, or diffused through the wood up to a ¼ inch from the surface of application. It was further visually determined that boron had penetrated the wood up to 1½ inches from the treated surface using AWPA Standard A3-08, Method 17, Standard Method for Determining Penetration of Boron-Containing Preservatives and Fire Retardants.

Example 9

A supplemental/remedial preservative paste composition was prepared by blending together in the order listed; 45.05 parts water, 3.00 parts of a fine copper dispersion comprised of 33.3% copper carbonate, 0.75 parts of a commercially available cellulose ether thickener, 43.70 parts sodium tetraborate decahydrate, and 7.50 parts attapulgite clay thickener. This remedial preservative paste contained 1.00 parts copper as derived from the fine copper carbonate dispersion for a weight ratio of 43.7 parts boron compound to 1.00 part copper.

Penetration testing performed on the paste composition formulated according to the example above showed a penetration of 220 tmm.

Further, the paste composition formulated according to the above example was brushed to 18 inches of the below-ground section of 10 utility-pole sections installed in a fieldtest plot located in Gainesville, Fla. The paste product was installed by an experienced preservative chemical applicator and was found to have desirable physical properties including viscosity, spreadability and adherence for application to in-service utility poles, cross-ties and other wooden structures.

Chemical penetration and retention was assessed at 12 months following treatment with the paste composition formulated according to the above example. Copper was detected at fungitoxic levels in the outer ¼ inch of the test poles at 12 months following treatment. Boron was detected at levels above the fungitoxic threshold level up to a depth of 3.0 inches from the pole surface after 12 months. Thus desirable chemical penetration and retention levels were obtained.

Example 10

A supplemental/remedial preservative paste composition is prepared by blending together in the order listed; 33.66 parts water, 0.04 parts bifenthrin, 0.10 parts tebuconazole, 6.00 parts of a fine copper dispersion comprised of 33.3% basic copper carbonate, 10.00 parts glycerin, 0.50 parts of a commercially available cellulose ether thickener, 21.85 parts sodium tetraborate decahydrate, 21.85 parts sodium fluoride, and 6.0 parts attapulgite clay thickener.

This remedial preservative paste contains 2.00 parts copper as derived from the fine basic copper carbonate dispersion for a weight ratio of 10.92 parts boron compound to 1.00 part copper and 10.92 parts fluoride compound to 1.00 part copper.

Example 11

A supplemental/remedial preservative paste composition was prepared by blending together in the order listed; 44.6 parts water, 3.00 parts of a fine copper dispersion comprised of 33.3% copper hydroxide, 0.70 parts pigmented dyes, 0.50 parts of a commercially available cellulose ether thickener, 43.70 parts boric acid, and 7.50 parts attapulgite clay thickener. This remedial preservative paste contained 1.0 parts copper as derived from the fine copper hydroxide dispersion for a weight ratio of 43.7 parts boron compound to 1.00 part copper.

Example 12

A supplemental/remedial preservative paste composition was prepared by blending together in the order listed; 44.6 parts water, 3.00 parts of a fine copper dispersion comprised of 33.3% copper hydroxide, 0.70 parts pigmented dyes, 0.50 parts of a commercially available cellulose ether thickener, 43.70 parts sodium fluoride, and 7.50 parts attapulgite clay thickener. This remedial preservative paste contained 1.0 parts copper as derived from the fine copper hydroxide dispersion for a weight ratio of 43.7 parts fluoride compound to 1.00 part copper.

Example 13

A supplemental/remedial preservative paste composition is prepared by blending together in the order listed; 41.79 parts water, 9.38 parts propylene glycol, 1.5 parts of a fine basic copper carbonate dispersion comprised of 33.3% copper, 0.33 parts didecyldimethylammonium carbonate/bicarbonate, 2.00 parts of a commercially available cellulose ether thickener, 36.0 parts disodium octaborate tetrahydrate, 2.0 part calcium sulfate filler and 7.0 parts attapulgite clay thickener.

This remedial preservative paste contains 0.50 parts copper as derived from the fine basic copper carbonate dispersion for a weight ratio of 72.00 parts boron compound to 1.00 part copper.

Example 14

A supplemental/remedial preservative paste composition was prepared by blending together in the order listed; 44.6 parts water, 3.00 parts of a fine copper dispersion comprised of 33.3% copper carbonate, 0.70 parts pigmented dyes, 0.50 parts of a commercially available cellulose ether thickener, 43.70 parts sodium tetraborate decahydrate, and 7.50 parts attapulgite clay thickener. This remedial preservative paste contained 1.0 parts copper as derived from the fine copper carbonate dispersion for a weight ratio of 43.7 parts boron compound to 1.00 part copper.

A series of preservative treating formulations were prepared by diluting the paste composition formulated according to the example above with water. The stable dispersions were used to treat southern pine test stakes measuring 0.75×0.75×0.75 inches by the full-cell process. Stable dispersions were prepared to vacuum-pressure treat the test blocks rather than apply the preservative paste to the surface of the pine test blocks, which may have acted as a barrier or strong repellent. The treated cubes were exposed to two common test fungi to evaluate the bio-efficacy of the preservative formulations following procedure described in AWPA Standard E10-12, Standard Method of Testing Wood Preservatives by Laboratory Soil-Block Cultures. Upon completion of the soil-block test, the cubes were found to have less than 2% weight loss, indicating essentially no fungal attack to the treated cubes. In comparison, untreated wood cubes had approximately 60% weight loss after being exposed to the test fungi.

Example 15

A series of preservative treating formulations were prepared by diluting the paste composition formulated according to Example 14 above with water. The stable dispersions were used to treat southern pine test stakes measuring 0.75×0.75×0.75 inches by the full-cell process. Stable dispersions were prepared to vacuum-pressure treat the test blocks rather than apply the preservative paste to the surface of the pine test blocks, which may have acted as a barrier or strong repellent. The treated cubes were exposed to termites to evaluate the resistance of the preservative formulations following the procedure described in AWPA Standard E1-12, Standard Method for Laboratory Evaluation to Determine Resistance to Subterranean Termites. Upon completion of the termite test, the cubes were found to have less than 5% weight loss with visual ratings of 8.2 to 9.4 (scale of 0 to 10, 0 being complete failure and 10 having no attack), indicating excellent protection against termite attack. In comparison, untreated wood cubes had approximately 35% weight loss and a visual rating of 3.8 after being exposed to the test termites.

Example 16

A supplemental/remedial preservative paste composition was prepared in accordance with Example 14. The paste composition was tested for volatile organic compounds (VOC) content in accordance with EPA Method 8620, Volatile Organic Compounds by Gas Chromatography Mass Spectrometry (GC/MS).

Two commercially available remedial preservative paste formulations were also tested for VOC content in accordance with EPA Method 24, SCAQMD 304 or Modified EPA Method 8620 (which are incorporated by reference in their entireties). The first commercially available paste formulation, known to contain an oil-borne copper naphthenate complex was analyzed to have a VOC content of 340 grams VOC/liter coating. The second commercial paste product was formulated according to U.S. Pat. No. 8,221,797, which contained a micronized form of oxine copper that had a VOC content of 36 grams VOC/liter coating. Testing of a remedial preservative paste composition made in accordance with the present invention was analyzed to have a non-detectable level of VOCs (0.1% LOD). An oil-borne copper naphthenate solution containing 2% copper was analyzed to have a VOC content of 698 grams VOC/liter coating. Consequently, a remedial preservative paste formulation that is essentially free of volatile organic compounds was achieved.

Example 17

The supplemental/remedial preservative paste composition of Example 14 was continuously extruded through a ½ inch diameter aperture and subsequently cut into 3 inch lengths. The rods were then dried at 90° F. for 24 hours. The resulting preservative rods were found to be structurally sound, uniformly shaped and preferable for insertion into predrilled holes such that are drilled into in-service utility poles, piling, cross-ties and other wooden structures for the afterprotection against wood destroying decay fungi. Further, the rods were placed on a wet sponge partially submerged in a water bath to allow continual wicking of water from the bath to the rod. After six weeks it was determined through analysis that the water bath contained appreciable levels of copper and boron. Consequently, a preservative rod composition was achieved.

Example 18

The supplemental/remedial preservative paste composition of Example 9 was injected into ⅜ inch holes drilled into an in-service utility pole containing a large decay void. The preservative paste formulation was found to be easily pumped or transferred with standard pneumatic pumping equipment or by gravity feed. The pole section containing the void was subsequently dissected and the paste composition was found to have completely filled the void and achieved intimate contact with the surfaces of the wood such that would provide adequate diffusion of biocide to the wood substrate in the presence of moisture or liquid water. Consequently, a preservative internal treatment composition was achieved.

Example 19

The supplemental/remedial preservative paste composition of Example 10 was rolled onto a polyethylene sheet to a uniform thickness of 0.0625 inches. The subsequent paste/support system was cut to 21 inches in length and applied to the below ground portion of an in-service utility pole such that the entire circumference of the pole was incased to 18 inches below ground. As the paste/support system was handled and transported the paste did not slump, run or drip off of the supporting material. Removal of the paste/support system from the pole shortly after application found that the paste composition adhered and maintained intimate contact with to the pole surface such that would provide adequate diffusion of the biocide to the wood substrate in the presence of moisture or liquid water. Consequently, a preservative wrap or bandage composition was achieved.

Example 20

The preservative penetration and retention characteristics in full-size southern pine pole sections initially treated with pentachlorophenol discovered from field testing the supplemental/remedial preservative paste composition formulated according to Example 9 above was compared to known commercially available paste formulations and associated third party generated penetration and retention data.

Chemical penetration and retention was assessed at 12 months following treatment with the paste composition formulated according to Example 9 above. Chemical penetration and retention may be measured by any method known in the art. Copper was detected at the fungitoxic level of 0.04 pounds per square foot (PCF) in the outer ¼ inch of the test poles at 12 months following treatment. The Oregon State University—Utility Pole Research Cooperative (OSU-UPRC) has established a threshold level for copper of 0.04 PCF when used in remedial preservative applications (OSU-UPRC 2013 Annual Report). This value also corresponds with the copper threshold retention level listed for copper naphthenate in AWPA Use Category 3B (AWPA 2013 Book of Standards).

The UPRC established a field trial in November 2004 to evaluate the performance of external supplemental preservative pastes on southern pine utility poles initially treated with pentachlorophenol. This study included 3 commercially available copper containing paste formulations each of which contained copper at 2% wt/wt that had been complexed, or solubilized with the use of organic solvents. Copper levels for Formulation A, a fuel oil based preservative paste that utilized an oil based naphthenic acid to complex the copper source, were found to be 70% in excess of the established copper threshold level of 0.04 PCF in the outer ¼ inch of the test poles. Copper levels for Formulation B, a water based preservative paste that utilized monoethanolamine to complex the copper source, were found to be 168% in excess of the established copper threshold level in the outer ¼ inch of the test poles. Copper levels for Formulation C, a water based preservative paste that utilized a water dispersible naphthenic acid to complex the copper source, were found to be 167% in excess of the established copper threshold level 0.04 PCF in the outer ¼ inch of the test poles. The data for Formulation C represents 2 year data as the 1 year data was unavailable.

The uncontrolled mobility of the copper component from current paste compositions as demonstrated from the UPRC study is a concern from a performance standpoint. Water- and oil-soluble copper complexes provide an uncontrolled dose to the wooden structure to be preserved that quickly disperses beyond the intended zone of protection within the wooden structure and rapidly depletes the copper reservoir contained within the residual paste composition diminishing the ability of the treatment to provide prolonged periods of protection from the action of decay and wood destroying insects such as termites. The amount of copper that is delivered by prior art formulations into the outer shell of the test poles is excessive and unnecessary as levels are far in excess of fungitoxic thresholds and a large degree of protection is also afforded by co-biocides in each of the formulations and by any residual chemical remaining in the poles from the initial preservative treatment.

The slow or controlled release of the micronized copper carbonate from the supplemental/remedial preservative paste composition made in accordance with this invention was an unexpected and surprising occurrence.

We claim:

1. An aqueous wood preservative paste composition comprising:
    a dispersion of solid particles of a substantially insoluble copper compound in an amount from 0.001% to 10% by weight of the paste composition;
    a boron-containing compound, a fluoride-containing compound, or a combination thereof; and
    an aqueous carrier;
    wherein the paste composition has a viscosity of 125 to 425 tenths of a millimeter (tmm) as measured using a penetrometer, and
    wherein at least 20% of the particles of the paste composition comprise particles having particle size greater than 25 microns.

2. The aqueous wood preservative paste composition of claim 1, wherein at least 30% of the particles of the paste composition comprise particles having particle size greater than 25 microns.

3. The aqueous wood preservative paste composition of claim 1, wherein less than 20% of the particles of the paste composition comprise particles having particle size greater than 100 microns.

4. The aqueous wood preservative paste composition of claim 1, wherein the paste composition contains from 1% to 5% copper atoms by weight of the paste composition.

5. The aqueous wood preservative paste composition of claim 1, wherein the copper compound comprises copper hydroxide, cupric oxide, cuprous oxide, copper carbonate, basic copper carbonate, copper oxychloride, dimethyldithiocarbamate, copper omadine, copper borate, or a combination thereof.

6. The aqueous wood preservative paste composition of claim 1, wherein the boron-containing compound comprises a boric acid, a metal borate, a sodium borate, a potassium borate, or a combination thereof.

7. A method for remedial treatment of wood, comprising applying the paste composition of claim 1 to a wooden structure.

8. The method of claim 7, wherein the wooden structure is an in-service wood product.

9. The method of claim 7, wherein the paste composition is applied onto or into the wooden structure.

10. The method of claim 8, wherein the in-service wood product is a utility pole, a railroad tie, or a wooden bridge.

11. A method comprising blending solid particles of a substantially insoluble copper compound; a boron-containing compound, a fluoride-containing compound, or a combination thereof; and an aqueous carrier to produce a paste composition, wherein at least 20% of the particles of the paste composition comprise particles having particle size greater than 25 microns.

12. The method of claim 11, wherein at least 30% of the particles of the paste composition comprise particles having particle size greater than 25 microns.

13. The method of claim 11, wherein the paste composition contains from 1% to 5% copper atoms by weight of the paste composition.

14. The method of claim 11, wherein the copper compound comprises copper hydroxide, cupric oxide, cuprous oxide, copper carbonate, basic copper carbonate, copper oxychloride, dimethyldithiocarbamate, copper omadine, copper borate, or a combination thereof.

15. The method of claim 11, wherein the boron-containing compound comprises a boric acid, a metal borate, a sodium borate, a potassium borate, or a combination thereof.

16. A method of delivering a fungitoxic amount of copper ion to an interior portion of a wooden product comprising:
applying an aqueous wood preservative paste composition comprising a dispersion of solid particles of a substantially insoluble copper compound in an amount of 0.001% to 10% by weight of the paste composition; a boron-containing compound, a fluoride-containing compound, or a combination thereof; and an aqueous carrier,
wherein the paste composition has a viscosity of between 125 and 425 tenths of a millimeter (tmm) as measured using a penetrometer;
wherein at least 30% of the particles of the paste composition comprise particles having particle size greater than 25 microns; and
wherein applying the paste composition to the wooden structure produces penetration of copper ions into an interior portion of the wooden structure to a fungicidally effective level.

17. The method of claim 16, wherein at least 40% of the particles of the paste composition comprise particles having particle size greater than 25 microns.

18. The method of claim 16, wherein the paste composition contains from 1% to 5% copper atoms by weight of the paste composition.

19. The method of claim 16, wherein the copper compound comprises copper hydroxide, cupric oxide, cuprous oxide, copper carbonate, basic copper carbonate, copper oxychloride, dimethyldithiocarbamate, copper omadine, copper borate, or a combination thereof.

20. The method of claim 16, wherein the boron-containing compound comprises a boric acid, a metal borate, a sodium borate, a potassium borate, or a combination thereof.

* * * * *